(12) United States Patent
Nunez et al.

(10) Patent No.: US 8,273,914 B1
(45) Date of Patent: Sep. 25, 2012

(54) PROCESS FOR PREPARING VINYL CHLOROFORMATE

(75) Inventors: Ivan M. Nunez, Penfield, NY (US); David E. Seelye, Williamsville, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 13/169,085

(22) Filed: Jun. 27, 2011

(51) Int. Cl.
*C07C 69/63* (2006.01)
(52) U.S. Cl. ........................................ 560/226
(58) Field of Classification Search .......... None
See application file for complete search history.

(56) References Cited

U.S. PATENT DOCUMENTS

| | | |
|---|---|---|
| 5,310,779 A | 5/1994 | Lai |
| 5,449,729 A | 9/1995 | Lai |
| 5,610,252 A | 3/1997 | Bambury et al. |
| 6,166,236 A | 12/2000 | Bambury et al. |
| 6,423,862 B1 | 7/2002 | Allen et al. |
| 7,402,689 B2 * | 7/2008 | Seelye et al. .................. 556/420 |
| 7,745,564 B2 | 6/2010 | Nandu et al. |
| 2006/0293481 A1 | 12/2006 | Seelye et al. |

* cited by examiner

*Primary Examiner* — Karl J Puttlitz
(74) *Attorney, Agent, or Firm* — John E. Thomas

(57) ABSTRACT

Disclosed is a process for making vinyl chloroformate which includes reacting (a) a carbonyl compound of formula I:

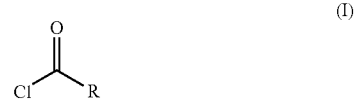

wherein R is a halogen or an alkyl group of 1 to about 25 carbon atoms; with (b) a silyl-containing enol ether and in the presence of an effective amount of a Group VIII-containing catalyst.

23 Claims, No Drawings

PROCESS FOR PREPARING VINYL CHLOROFORMATE

BACKGROUND OF THE INVENTION

1. Technical Field

The present invention generally relates to a process for preparing vinyl chloroformate and its use in making biomedical devices.

2. Description of Related Art

Vinyl chloroformate (VCF) is used as a starting raw material for the synthesis of many medical devices such as those disclosed in, for example, U.S. Pat. Nos. 5,310,779, 5,449,729, 5,610,252 and 6,166,236, the contents of which are incorporated herein by reference. For example, two of the key monomers used in the production of hydrogel contact lenses are (N-vinyloxycarbonyl)-3-aminopropyltris(trimethylsiloxysilane) (RD325) and vinylcarbamate-capped polydimethylsiloxane (RD352). The current synthesis of RD325 consists of reacting VCF with aminopropyltris(trimethylsiloxysilane). The current synthesis of RD352 involves a triflic acid catalyzed ring opening polymerization of octamethylcyclotetrasiloxane with a vinyl carbamate butyl-capped tetramethyldisiloxane (V2). V2 is prepared by the reaction of VCF with 1,3-(4-hydroxybutyl)-1,1,3,3-tetramethyldisiloxane. Both syntheses are relatively straightforward and result in a high yield of product. A significant drawback, however, of both reactions is that the monomer VCF is used.

Currently, it is believed that VCF is only available via a multi-step synthesis which involves the use of phosgene and organomercury reagents. However, organomercury reagents are undesirable in that they present heightened environmental concerns.

Accordingly, efforts have been made to avoid the use of VCF in making medical devices such as contact lenses. For example, U.S. Pat. No. 6,423,862 discloses a multi-step method for making a vinyl carbamate that does not necessitate the use of phosgene and organomercury intermediates. Another example is U.S. Pat. No. 7,402,689 which discloses methods of forming vinyl(thio)carbamates and more particularly to a vinylchloroformate-free method of synthesizing (N-vinyloxycarbonyl)-3-aminopropyltris(trimethylsiloxysilane). Yet another example is U.S. Pat. No. 7,745,564 which discloses a method of synthesizing device forming monomers using N-(vinyloxycarbonyloxy)succinimide. However, additional methods of making vinyl or allyl(thio)carbamates that do not require the use of organomercury reagents and are relatively straightforward are still needed.

Accordingly, it would be desirable to provide an improved process for making vinyl chloroformate in a simple, cost effective manner that does not involve the use of organomercury reagents.

SUMMARY OF THE INVENTION

In accordance with one embodiment of the present invention, there is provided a process for making vinyl chloroformate which comprises reacting (a) a carbonyl compound of formula I:

wherein R is a halogen or an alkyl group of 1 to about 26 carbon atoms; with (b) a silyl-containing enol ether and in the presence of an effective amount of a Group VIII metal-containing catalyst.

In accordance with a second embodiment of the present invention, there is provided a process for making vinyl chloroformate which comprises reacting (a) phosgene with (b) a silyl-containing enol ether of the general formula:

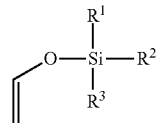

wherein $R^1$, $R^2$ and $R^3$ are independently a substituted or unsubstituted, straight or branched $C_1$ to $C_9$ alkyl group in the presence of an effective amount of a Group VIII metal-containing catalyst.

In accordance with a third embodiment of the present invention, there is provided a process for making vinyl chloroformate which comprises reacting (a) phosgene with (b) a silyl-containing enol ether of the general formula:

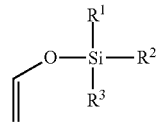

wherein $R^1$, $R^2$ and $R^3$ are independently a substituted or unsubstituted, straight or branched $C_1$ to $C_9$ alkyl group and in the presence of an effective amount of a palladium-containing catalyst or a platinum-containing catalyst.

The processes of the present invention advantageously synthesize VCF in a relatively high yield without the need to use highly toxic organomercury reagents. Accordingly, the process of the present invention is environmentally friendly and does not require extensive and costly purification procedures to remove unwanted by-products and unreacted organomercury reagants. In this manner, VCF can be synthesized in a simple, cost efficient process.

DETAILED DESCRIPTION OF THE PREFERRED EMBODIMENTS

The present invention is directed to a process for making vinyl chloroformate. In general, the process involves reacting (a) a carbonyl compound of formula I:

wherein R is a halogen or an alkyl group of 1 to about 26 carbon atoms with (b) a silyl-containing enol ether and in the presence of an effective amount of a Group VIII-metal containing catalyst.

Suitable halogens include bromine, chlorine, and the like. In one embodiment, R is chlorine.

Representative examples of alkyl groups for use as R for the carbonyl compound of the formula I include, by way of example, a straight or branched hydrocarbon chain radical containing carbon and hydrogen atoms of from 1 to about 26 carbon atoms, to the rest of the molecule, e.g., methyl, ethyl, n-propyl, 1-methylethyl (isopropyl), n-butyl, n-pentyl, etc., and the like. In one embodiment, examples of alkyl groups for use herein include a straight or branched hydrocarbon chain radical containing carbon and hydrogen atoms of from 1 to about 12 carbon atoms. In one embodiment, examples of alkyl groups for use herein include a straight or branched hydrocarbon chain radical containing carbon and hydrogen atoms of from 1 to about 6 carbon atoms.

In one embodiment, R is a fatty acid moiety, which can be is a straight chain, saturated or unsaturated hydrocarbon group containing from about 4 to about 26 carbon atoms, e.g., caprylic group, caproic group, capric group, myristic group, palmitic group, palmitoleic group, stearic group, oleic group, linoleic group, linolenic group, arachidic group, eicosenoic group, behenic group, lignoceric group, tetracosenic group, etc. and combinations thereof.

Silyl-containing enol ethers for use in the process of the present invention can be any known silyl-containing enol ether. In one embodiment, a class of silyl-containing enol ethers is represented by the compound of formula II:

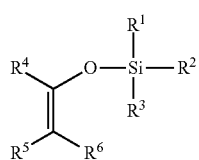

(II)

wherein $R^1$, $R^2$ and $R^3$ are independently a hydrocarbyl group of 1 to about 30 carbon atoms and $R^4$, $R^5$ and $R^6$ are independently hydrogen or a $C_1$ to $C_6$ alkyl group.

Suitable hydrocarbyl groups includes, by way of example, a substituted or unsubstituted, straight or branched $C_1$ to $C_{30}$ alkyl group, a substituted or unsubstituted $C_3$ to $C_{30}$ cycloalkyl group, a substituted or unsubstituted $C_3$ to $C_{30}$ cycloalkylalkyl group, a substituted or unsubstituted $C_3$ to $C_{30}$ cycloalkenyl group, a substituted or unsubstituted $C_5$ to $C_{30}$ aryl group, or a substituted or unsubstituted $C_5$ to $C_{30}$ arylalkyl group.

Representative examples of alkyl groups for use herein include, by way of example, a straight or branched hydrocarbon chain radical containing carbon and hydrogen atoms of from 1 to about 30 carbon atoms, to the rest of the molecule, e.g., methyl, ethyl, n-propyl, 1-methylethyl (isopropyl), n-butyl, n-pentyl, etc., and the like. In one embodiment, examples of alkyl groups for use herein include a straight or branched hydrocarbon chain radical containing carbon and hydrogen atoms of from 1 to about 12 carbon atoms. In one embodiment, examples of alkyl groups for use herein include a straight or branched hydrocarbon chain radical containing carbon and hydrogen atoms of from 1 to about 9 carbon atoms. In one embodiment, examples of alkyl groups for use herein include a straight hydrocarbon chain radical containing carbon and hydrogen atoms of from 1 to 6 carbon atoms.

Representative examples of cycloalkyl groups for use herein include, by way of example, a substituted or unsubstituted non-aromatic mono or multicyclic ring system of about 3 to about 30 carbon atoms or about 3 to about 12 carbon atoms such as, for example, cyclopropyl, cyclobutyl, cyclopentyl, cyclohexyl, perhydronapthyl, adamantyl and norbornyl groups; bridged cyclic group or spirobicyclic groups, e.g., spiro-(4,4)-non-2-yl and the like, optionally containing one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms or about 3 to about 12 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms or about 3 to about 12 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms or about 5 to about 12 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

In one embodiment, $R^1$, $R^2$ and $R^3$ are independently a substituted or unsubstituted, straight or branched $C_1$ to $C_9$ alkyl group. In another embodiment, $R^1$, $R^2$ and $R^3$ are independently an alkyl group of 1 to about 9 carbon atoms and $R^4$, $R^5$ and $R^6$ are hydrogen.

In one embodiment, a class of silyl-containing enol ethers is represented by the compound of formula III:

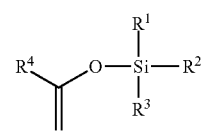

(III)

wherein $R^1$, $R^2$, $R^3$ and $R^4$ have the aforestated meanings. In one embodiment, $R^1$, $R^2$ and $R^3$ are independently a substituted or unsubstituted, straight or branched $C_1$ to $C_9$ alkyl group. In another embodiment, $R^1$, $R^2$ and $R^3$ are independently an alkyl group of 1 to about 9 carbon atoms and $R^4$ is methyl.

In one preferred embodiment, a class of silyl-containing enol ethers is represented by the compound of formula IV:

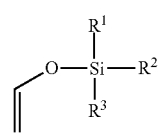

(IV)

wherein $R^1$, $R^2$ and $R^3$ are independently a hydrocarbyl group of 1 to about 30 carbon atoms.

Representative examples of silyl-containing enol ethers of formula IV include:

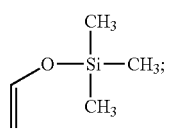

Vinyloxytrimethylsilane (VOTMS)

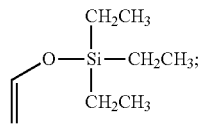

Vinyloxytriethylsilane (VOTES)

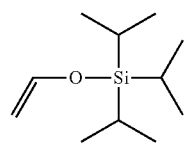

Vinyloxytriisopropylsilane (VOTIPS)

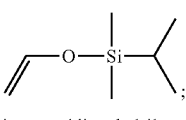

Vinyloxyisopropyldimethylsilane (VOIPDMS)

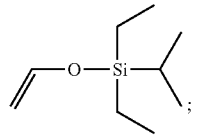

Vinyloxydiethylisopropylsilane (VODEIPS)

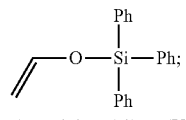

Vinyloxytriphenylsilane (VOTPS)

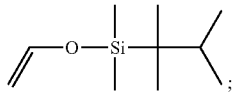

Vinyloxydimethylthexylsilane (VODMTS)

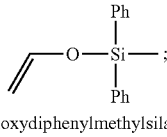

Vinyloxydiphenylmethylsilane (VODPMS)

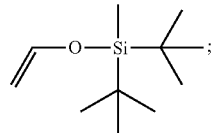

Vinyloxyditbutylmethylsilane (VODBMS)

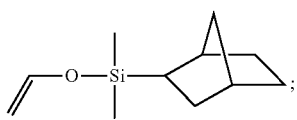

Vinyloxy2-norbonyldimethylsilane (VONDMS)

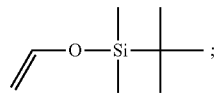

Vinyloxy t-butyldimethylsilane (VOTBDMS)

-continued

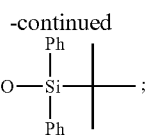

Vinyloxy t-butyldiphethylsilane (VOTBDPS)

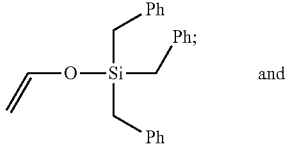    and

Vinyloxytribenzylsilane (VOTBS)

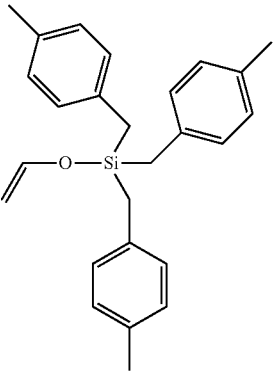

Vinyloxytrixylylsilane (VOTXS)

In one preferred embodiment, a process for making vinyl chloroformate involves reacting (a) a carbonyl compound of the formula:

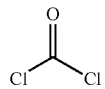

with (b) a silyl-containing enol ether of the formula:

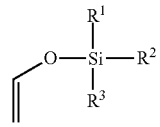

wherein $R^1$, $R^2$ and $R^3$ are independently a substituted or unsubstituted, straight or branched $C_1$ to $C_9$ alkyl group and in the presence of a Group VIII-containing catalyst.

In general, a carbonyl compound of formula I is reacted with a silyl-containing enol ether in a molar ratio of carbonyl compound of formula I to silyl-containing enol ether ranging from about 1:1 to about 1:3. In one embodiment, a carbonyl compound of formula I is reacted with a silyl-containing enol ether in a molar ratio of carbonyl compound of formula I to silyl-containing enol ether ranging from about 1:1.05 to about 1:1.25.

The reaction of a carbonyl compound of formula I with a silyl-containing enol ether is carried out in the presence of a Group VIII-metal containing catalyst. Suitable Group VIII metal-containing catalyst include those based on iron, ruthenium, osmium; cobalt, rhodium, iridium; nickel, copper, silver, gold, nickel, palladium and platinum. In one preferred embodiment, suitable Group VIII metal-containing catalysts include complexes based on palladium or platinum. In another preferred embodiment, a suitable Group VIII metal-containing catalyst is a palladium complex.

The palladium-containing catalysts suitable for the reaction of a carbonyl compound of formula I with a silyl-containing enol ether are generally palladium (II) or palladium (0) complexes. Representative examples of such catalysts include tetrakis(triphenylphosphine)palladium (0), bis(benzonitrile)palladium (II) chloride, palladium (II) trifluoroacetate, palladium (II) dichloride, sodium tetrachloro palladium (II), dichlorobis(triphenylphosphine)palladium (II), palladium (II) acetate and the like and mixtures thereof. In one preferred embodiment, the palladium-containing catalyst is a palladium(II) complex.

In one embodiment, the palladium catalyst can also be prepared in situ from palladium(II) or palladium(0) compounds by complexing with the desired ligands. For example, a palladium(II) salt that is to be complexed, e.g., palladium (II) dichloride ($PdCl_2$) or palladium(II) acetate ($Pd(OAc)_2$), together with the desired ligand, e.g., triphenylphosphine ($PPh_3$) or tricyclohexylphosphine ($PCy_3$), can be placed in the reaction mixture of carbonyl compound of formula I with a silyl-containing enol ether. Palladium(II) dichloride can be used as an inexpensive palladium salt also in the form of a 20% $PdCl_2$ solution in concentrated hydrochloric acid. The desired ligand is advantageously added to the reaction mixture in an excess of up to about 10 mol in relation to the palladium salt. The is formed in situ the palladium (II) or palladium (0) complex desired for the coupling reaction of the carbonyl compound of formula I with the silyl-containing enol ether, which complex then initiates the coupling reaction.

In one embodiment, examples of ligands suitable for palladium (II) and palladium(0) complexes include trimethylphosphine, triethylphosphine, tris(tert-butyl)phosphine, tricyclopentylphosphine, tricyclohexylphosphine ($PCy_3$), tri (methylcyclohexyl)phosphine, methyl(tetramethylene)phosphine, tert-butyl(pentamethylene)phosphine, triphenylphosphine ($PPh_3$), tri(methylphenyl)phosphine, 1,2-diphenylphosphinecyclohexane, 1,2-diphenylphosphinecyclopentane, 2,2'-(diphenylphosphine)-biphenyl, 1,2-bis(diphenylphosphine)ethane, 1,3-bis (diphenylphosphine)propane, 1,4-bis(diphenylphosphine) butane, 3,4-bis(diphenylphosphine)pyrrolidine, 2,2'-(diphenylphosphine)-bisnaphthyl (Binap), 1,1'-bis (diphenylphosphine)ferrocene, 1,1'-bis(di-tert-butylphosphine)ferrocene, and the like.

In another embodiment, an example of ligands suitable for palladium (II) and palladium (0) complexes is bidentate nitrogen ligands. Representative examples of such bidentate nitrogen ligands include, but are not limited to, bidentate nitrogen ligands of the following formulae:

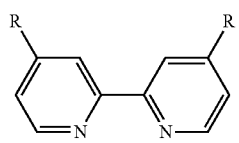

R = H, $CH_3$, 5-nonyl, n-heptyl, $CO_2Me$

-continued

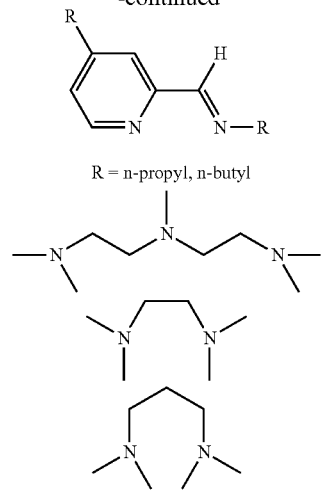

R = n-propyl, n-butyl

The platinum-containing catalysts suitable for the reaction of a carbonyl compound of formula I with a silyl-containing enol ether are generally platinum (0) and platinum complexes. Representative examples of such catalysts include platinum (0) 1,3-divinyl-1,1,3,3-tetramethyldisiloxane complex in xylene, and platinum acetylacetonate.

If desired, the metal catalyst is dispersed on or bonded to at least one support material. A wide variety of support materials are known as suitable in the art and include, but are not limited to, support materials comprising carbon, activated charcoal, silica, alumina, titania, zirconia, a zeolite, a polymer, Group II-containing carbonates and sulfates such as calcium carbonate, barium carbonate, calcium sulfate or barium sulfate. When the support material is a polymer, it is preferably an organic polymer or resin having functional groups suitable for bonding to the transition metal salt or complex.

In the embodiments where the metal catalyst is supported, the transition metal, transition metal salt, or transition metal complex comprises from about 0.1 to about 10 weight percent, based on the weight of the support material.

An effective amount of the catalyst is an amount effective to react the carbonyl compound of formula I with the silyl-containing enol ether. In general, the catalyst is employed in an effective amount ranging from about 0.001 mole % to about 25 mole % relative to the silyl-containing enol ether (e.g., VOTMS). In one embodiment, the catalyst is employed in an effective amount ranging from about 0.05 mole % to about 0.1 mole % relative to the silyl-containing enol ether (e.g., VOTMS).

In one embodiment, the reaction of a carbonyl compound of formula I with a silyl-containing enol ether is advantageously carried out in the presence of a non-aliphatic hydrocarbon solvent. Representative examples of suitable non-aliphatic hydrocarbon solvents include, but are not limited to, ether-containing solvents, nitrile-containing solvents, aromatic hydrocarbon-containing solvents, cyclic urea-containing solvents and the like. Suitable ether-containing solvents include, but are not limited to, 2-methoxyethylether, ethyleneglycol diethyl ether, dibutyl ether, tri(ethylene glycol) dimethyl ether, tetra(ethylene glycol) dimethyl ether, di(ethylene glycol) dibutyl ether, low molecular weight polyethylene glycols such as polyethylene glycol 400, 600, and 1000 and the like and mixtures thereof. Suitable nitrile-containing solvents include, but are not limited to, acetonitrile, adiponitrile, cyclopentanecarbonitrile cyclohexanecarbonitrile, and the like. Suitable aromatic hydrocarbon-containing solvents include benzene which may have a substitutional group (e.g., $C_1$ to $C_6$ alkyl group, $C_1$ to $C_6$ alkoxy group, nitro group, nitrile group, halogen group or the like), and specific examples of the aromatic hydrocarbon solvent include toluene, xylene, benzene, nitrobenzene, benzonitrile and the like. Suitable cyclic urea-containing solvents include, but are not limited to, 1,3-dimethyl-2-imidazolidinone and the like.

In general, the solvent is ordinarily present in an amount ranging from about 2 mL solvent to about 1 gram of silyl-containing enol ether to about 15 mL of solvent to 1 gram of silyl-containing enol ether. In one embodiment, the solvent is present in an amount of from about 5 mL of solvent to about 1 gram of silyl-containing enol ether.

When a solvent is employed in the reaction, the resulting solution containing VCF may be used as is or the VCF can be extracted by a liquid/liquid extraction step using an aliphatic hydrocarbon solvent such as pentane or heptane. The extracted VCF may then be isolated by conventional techniques, e.g., distillation.

The reaction of a carbonyl compound of formula I with a silyl-containing enol ether is generally carried out at a temperature ranging from about −5° C. to about 25° C. and at a pressure of up to about 1 bar. In one embodiment, the reaction is carried out at a temperature ranging from about −2° C. to about 2° C. The time period for the reaction will ordinarily range from about 38 to about 48 hours.

If necessary, a polymerization inhibitor may be added to the reaction mixture in order to prevent polymerization of the silyl-containing enol ether or the resulting VCF. Representative examples of such polymerization inhibitors include 2,5-di-t-butylhydroquinone, 1,2,4-trihydroxybenzene, 2,5-bistetramethylbutylhydroquinone, leucoquinizarin, N,N'-di-2-naphthyl-p-phenylenediamine, N,N'-dinaphthyl-p-phenylenediamine, 4,4'-bis(.alpha.,.alpha.'-dimethylbenzyl)diphenylamine, 4,4'-dicumyl-diphenylamine, 2,2'-methylenebis(4-methyl-6-tert-butylphenol), N-(1-methylheptyl)-N'-phenyl-p-phenylenediamine, phenothiazine, 2-methoxyphenothiazine, tetraethylthiuram disulfide, 1,1-diphenyl-2-picrylhydrazyl, 1,1-diphenyl-2-picrylhydrazine, N-nitrosophenylhydroxylamine, aluminum salt of N-nitrosophenylhydroxylamine and the like.

The polymerization inhibitor is generally used in a total amount of from about 0.01 to about 1% by weight, based on the reaction mixture.

The VCF prepared according to the present invention is used, for example, in preparing device-forming monomers for use in forming biomedical devices. Examples of device forming monomers that can be synthesized using VCF include (N-vinyloxycarbonyl)-3-aminopropyltris(trimethylsiloxysilane) (RD325), vinylcarbamate-capped polydimethylsiloxane (RD352), Vinal acid (RD-594) and HEMA-VC (RD-678). For example, synthesis of RD325 involves reacting VCF with aminopropyltris(trimethylsiloxysilane), while the synthesis of RD352 involves a triflic acid catalyzed ring opening polymerization of octamethylcyclotetrasiloxane with a vinyl carbamate butyl-capped tetramethyldisiloxane (V2). V2 is prepared by the reaction of VCF with 1,3-(4-hydroxybutyl)-1,1,3,3-tetramethyldisiloxane. Both syntheses are relatively straightforward and can result in a high yield of product. Representative examples of biomedical devices which can then be formed include contact lenses, phakic intraocular lenses, aphakic intraocular lenses, corneal implants, and the like.

The following examples are provided to enable one skilled in the art to practice the invention and are merely illustrative of the invention. The examples should not be read as limiting the scope of the invention as defined in the claims.

EXAMPLES 1-30

General Procedure for Catalyst Evaluation
(Examples 1-30)

A 125 mL Eurostyle jacketed 3 neck flask was fitted with a cooling circulator (set at −2° C.), a magnetic stirring bar, a 25 mL graduated dropping funnel containing 15 mL of adiponitrile (topped with a dry ice condenser), and a gas outlet. A total of 11.6 grams (0.1 mole) of VOTMS, 0.0005 mol of catalyst and 75 mL of adiponitrile were charged to the flask. The reagents were stirred for 30 minutes. Subsequently, 7.9 mL (10.9 grams, 0.11 mol) of phosgene was condensed into the 25 mL dropping funnel. The phosgene was then added to the pot over a period of 3 minutes. The reaction was then allowed to proceed, while stirring, for 24 hours. Gas Chromatography (GC) samples were taken periodically, by filtering through a Glass Fiber Filter paper plug in a glass pipette.

The catalyst used in each of Examples 1-30 and the effect of the catalyst on the reaction yield is set forth below in Table 1.

TABLE 1

| Catalyst | Example | Yield, GC | Time, hrs |
|---|---|---|---|
| $Cd(Ac)_2$ hydrate dried at 160° C. | 1 | 0.0% | 6 |
| $Ni(II)Ac_2$ hydrate dried at 160° C. | 2 | 0.0% | 6 |
| Cu(i)Ac hydrate dried at 160° C. | 3 | 0.0% | 24 |
| $Cu(II)Ac_2$ | 4 | 0.0% | 24 |
| $Fe(III)Acac_3$ | 5 | 0.0% | 24 |
| AgAc | 6 | 0.0% | 24 |
| tetrakis(triphenylphosphine) Pd (0) | 7 | 20.7% | 24 |
| tetrakis(triphenylphosphine) Ni (0) | 8 | 0.0% | 24 |
| tetrakis(triphenylphosphine) Pt (0) | 9 | 0.0% | 24 |
| Pt (0) 1,3-divinyl hydrosilation cat | 10 | 17.2% | 24 |
| $Ni(II)Cl_2$ | 11 | 0.0% | 24 |
| $Zn(Ac)2$ hydrate dried at 160° C. | 12 | 0.0% | 24 |
| AgCl | 13 | 0.0% | 24 |
| $Pd(II)Cl_2$ | 14 | 35.1% | 24 |
| $Pd(II)TFA_2$ | 15 | 53.0% | 26 |
| bis(benzonitrile)Pd (II) chloride | 16 | 32.5% | 26 |
| sodium tetrachloroPd (II) | 17 | 30.1% | 24 |
| rhodium (III) chloride | 18 | 0.0% | 24 |
| rubidium acetate | 19 | 0.0% | 24 |
| chlorotris(triphenylphosphine) Rhodium I | 20 | 0.0% | 24 |
| platinum acac | 21 | 0.0% | 24 |
| tris(triphenylphosphine)ruthenium (II) chloride | 22 | 0.0% | 24 |
| dichlorobis(triphenyphosphine)Pd (II) | 23 | 20.7% | 24 |
| $Pd(Ac)_2$ | 24 | 58.3% | 24 |
| $CoAc_2$ | 25 | 0.0% | 24 |
| Co(II) 2,4-pentanedionate | 26 | 0.0% | 24 |
| Co(III) 2,4-pentanedionate | 27 | 0.0% | 24 |
| $Cu(II)TFA_2$ | 28 | 0.0% | 24 |
| $Hg(TFA)_2$ | 29 | 0.0% | 24 |
| AgTFA | 30 | 0.0% | 24 | adiponitrile with catalyst load 0.05%

Example 31

A series of solvents were evaluated using $Pd(OAc)_2$ as a catalyst. The solvents were used in Methods A and B as described below.

Method A

To a 3-neck 125 ml jacketed flask fitted with a magnetic stir bar, graduated dropping funnel topped with a dry ice condenser, gas outlet, and maintained at −2° C. were added 11.6 grams (100 mmole) vinyloxytrimethylsilane (VOTMS), and 0.11 grams (0.5 mmol) palladium acetate (PdOAc$_2$). The two reagents were stirred for 30 minutes with 75 mL of adiponitrile. A total of 7.9 mL (10.88 grams, 110 mmol) of phosgene was condensed and added to the reaction mixture. Gas Chromatography (GC) samples were taken periodically, and the reaction progress followed. The GC yield of VCF after 26 hours was found to be 48.6% and did not improve by extending the reaction time to 120 hours.

Method B

To a 3-neck 125 ml jacketed flask fitted with a magnetic stir bar, graduated dropping funnel topped with a dry ice condenser, gas outlet, and maintained at −2° C. were added 7.9 mL (10.88 grams, 110 mmol) of phosgene, 0.11 grams (0.5 mmol) of PdAc$_2$, and 75 mL of adiponitrile. VOTMS (11.6 grams, 100 mmole) in 13.5 mL of adiponitrile (2 phases) was added slowly over a period of 11.5 minutes to the reaction flask. The reaction was stirred and GC samples taken periodically to monitor yield of VCF. The GC yield of VCF after 26 hours was 43.6%, and was not observed to improve by extending the reaction time to 120 hours.

Table 2 below shows the effect of different solvents on the reaction yield for Methods A and B.

TABLE 2

| Solvent | Synthetic Method A | | Synthetic Method B | |
|---|---|---|---|---|
| | Yield, GC | Time, hrs | Yield, GC | Time, hrs |
| 2-methoxyethylether | 23.8% | 1 | 25.7% | 1 |
| ethyleneglycol diethyl ether | 20.4% | 1 | 26.4% | 3 |
| Adiponitrile | 48.6% | 26 | 43.6% | 26 |
| Decane | trace | 22 | trace | 22 |
| Xylenes | 25.9% | 22 | 26.1% | 22 |
| dibutyl ether | 12.6% | 22 | 11.8% | 22 |
| tri(ethylene glycol) dimethyl ether | 24.2% | 23 | 23.7% | 7 |
| tetra(ethylene glycol) dimethyl ether | 23.2% | 7 | 23.4% | 7 |
| di(ethylene glycol) dibutyl ether | 24.0% | 96 | 24.0% | 96 |
| Benzonitrile | 22.0% | 7 | 21.1% | 7 |
| Nitrobenzene | 23.8% | 3 | 22.6% | 23 |
| 1,3-dimethyl-2-imidazolidinone | 19.2% | 23 | 11.6% | 23 |

Pd(Ac)$_2$ catalyst at 0.05% load

Example 32

To a 2 L jacketed 3-neck flask fitted with a −2° C. chiller unit, mechanical stirrer with Teflon paddle, graduated dropping funnel with 213.3 grams adiponitrile topped with a dry ice condenser, and a gas outlet, was added 637 grams of adiponitrile, 116 grams (1.0 mole) VOTMS, and 1.7 grams (0.0075 mol) PdAc$_2$. The reagents were stirred for 30 minutes. Next, 112 grams, (1.1 mol) of phosgene was condensed into the dropping funnel with 213.3 grams of adiponitrile. The phosgene was added to the pot over a period of 63 minutes so the temperature was −2° C. to +2° C. The reaction mixture was allowed to stir and after 63 hours the reaction mixture was sparged with dry N$_2$ to remove excess phosgene, filtered to remove catalyst, and tert-butylhydroquinone was added to inhibit polymerization. A total of 1015 grams of 8.94% VCF solution was obtained from the reaction and provided 85.2% yield of VCF.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A process for making vinyl chloroformate, the process comprising reacting (a) a carbonyl compound of formula I:

wherein R is a halogen or an alkyl group of 1 to about 26 carbon atoms; with (b) a silyl-containing enol ether of formula II and in the presence of an effective amount of a Group VIII metal-containing catalyst

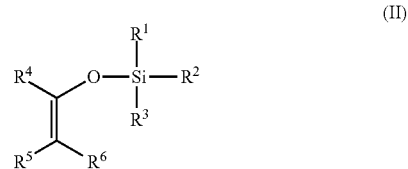

wherein $R^1$, $R^2$ and $R^3$ are independently a hydrocarbyl group of 1 to about 30 carbon atoms and $R^4$, $R^5$ and $R^6$ are independently hydrogen or a $C_1$ to $C_6$ alkyl group.

2. The process of claim 1, wherein the hydrocarbyl groups is a substituted or unsubstituted, straight or branched $C_1$ to $C_{30}$ alkyl group, a substituted or unsubstituted $C_3$ to $C_{30}$ cycloalkyl group, a substituted or unsubstituted $C_3$ to $C_{30}$ cycloalkylalkyl group, a substituted or unsubstituted $C_3$ to $C_{30}$ cycloalkenyl group, a substituted or unsubstituted $C_5$ to $C_{30}$ aryl group, or a substituted or unsubstituted $C_5$ to $C_{30}$ arylalkyl group.

3. The process of claim 1, wherein R is Cl, $R^1$, $R^2$ and $R^3$ are independently a substituted or unsubstituted, straight or branched $C_1$ to $C_9$ alkyl group and $R^4$, $R^5$ and $R^6$ are hydrogen.

4. The process of claim 1, wherein the carbonyl compound of formula I is reacted with the silyl-containing enol ether in a molar ratio of the carbonyl compound of formula I to the silyl-containing enol ether ranging from about 1:1 to about 1:3.

5. The process of claim 1, wherein the Group VIII metal-containing catalyst comprises a palladium-containing catalyst or a platinum-containing catalyst.

6. The process of claim 1, wherein the Group VIII metal-containing catalyst comprises a palladium-containing catalyst.

7. The process of claim 6, wherein the palladium-containing catalyst comprises a palladium (0) or palladium (II)-containing catalyst.

8. The process of claim 6, wherein the palladium-containing catalyst is selected from the group consisting of tetrakis (triphenylphosphine)palladium (0), bis(benzonitrile)palladium (II) chloride, palladium (II) trifluoroacetate, palladium (II) dichloride, sodium tetrachloro palladium (II), dichlorobis(triphenylphosphine)palladium (II), palladium (II) acetate and mixtures thereof.

9. The process of claim 1, wherein the effective amount of the Group VIII-containing catalyst is from about 0.001 mole % to about 25 mole % relative to the silyl-containing enol ether.

10. The process of claim 1, wherein the reaction takes place in the presence of a non-aliphatic hydrocarbon-containing solvent.

11. The process of claim 1, wherein the non-aliphatic hydrocarbon-containing solvent is selected from the group consisting of an ether-containing solvent, a nitrile-containing solvent, an aromatic hydrocarbon-containing solvent, a cyclic urea-containing solvent and mixtures thereof.

12. The process of claim 11, wherein the ether-containing solvent is selected from the group consisting of 2-methoxyethylether, ethyleneglycol diethyl ether, dibutyl ether, tri(ethylene glycol) dimethyl ether, tetra(ethylene glycol) dimethyl ether, di(ethylene glycol) dibutyl ether and mixtures thereof.

13. The process of claim 11, wherein the nitrile-containing solvent is selected from the group consisting of acetonitrile, adiponitrile, cyclopentanecarbonitrile, cyclohexanecarbonitrile and mixtures thereof.

14. The process of claim 11, wherein the aromatic hydrocarbon-containing solvent is selected from the group consisting of toluene, xylene, benzene, nitrobenzene, benzonitrile and mixtures thereof.

15. The process of claim 11, wherein the cyclic urea-containing solvent is 1,3-dimethyl-2-imidazolidinone.

16. A process for making vinyl chloroformate, the process comprising reacting (a) a carbonyl compound of the formula:

with (b) a silyl-containing enol ether of the formula:

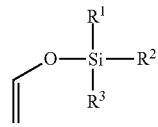

wherein $R^1$, $R^2$ and $R^3$ are independently a substituted or unsubstituted, straight or branched $C_1$ to $C_9$ alkyl group and in the presence of a palladium-containing catalyst or a platinum-containing catalyst.

17. The process of claim 16, wherein $R^1$, $R^2$ and $R^3$ are methyl.

18. The process of claim 16, wherein the carbonyl compound of formula I is reacted with the silyl-containing enol ether in a molar ratio of the carbonyl compound of formula I to the silyl-containing enol ether ranging from about 1:1 to about 1:3.

19. The process of claim 16, wherein the palladium-containing catalyst is selected from the group consisting of tetrakis(triphenylphosphine)palladium (0), bis(benzonitrile) palladium (II) chloride, palladium (II) trifluoroacetate, palladium (II) dichloride, sodium tetrachloro palladium (II), dichlorobis(triphenylphosphine)palladium (II), palladium (II) acetate and mixtures thereof.

20. The process of claim 16, wherein the effective amount of the palladium-containing catalyst is from about 0.001 mole % to about 25 mole % relative to the silyl-containing enol ether.

21. The process of claim 16, wherein the reaction takes place in the presence of a non-aliphatic hydrocarbon-containing solvent.

22. The process of claim 21, wherein the non-aliphatic hydrocarbon-containing solvent is a nitrile-containing solvent.

23. The process of claim 21, wherein the non-aliphatic hydrocarbon-containing solvent is selected from the group consisting of 2-methoxyethylether, ethyleneglycol diethyl ether, dibutyl ether, tri(ethylene glycol) dimethyl ether, tetra(ethylene glycol) dimethyl ether, di(ethylene glycol) dibutyl ether, acetonitrile, toluene, xylene, benzene, nitrobenzene, benzonitrile, 1,3-dimethyl-2-imidazolidinone and mixtures thereof.

\* \* \* \* \*